United States Patent
Levine et al.

(10) Patent No.: US 10,123,860 B2
(45) Date of Patent: Nov. 13, 2018

(54) CLOSED SYSTEM MOUTHPIECE WITH LIGHT AND HEAT GENERATION TO ACTIVATE A FORMULATION TO INCREASE ITS VOLUME

(71) Applicant: JBL RADICAL INNOVATIONS, LLC, New York, NY (US)

(72) Inventors: Jonathan B. Levine, New York, NY (US); Owen J. Murray, Far Hills, NJ (US); Elmar A. Dave, Clifton, NJ (US)

(73) Assignee: JBL Radical Innovations, LLC

( * ) Notice: Subject to any disclaimer, the term of this patent is extended or adjusted under 35 U.S.C. 154(b) by 0 days.

(21) Appl. No.: 15/403,459

(22) Filed: Jan. 11, 2017

(65) Prior Publication Data

US 2017/0224455 A1  Aug. 10, 2017

Related U.S. Application Data

(62) Division of application No. 13/956,787, filed on Aug. 1, 2013, now Pat. No. 9,572,645.

(51) Int. Cl.
| | |
|---|---|
| *A61C 19/06* | (2006.01) |
| *A61B 5/145* | (2006.01) |
| *A61B 5/00* | (2006.01) |
| *A61C 5/90* | (2017.01) |
| *A61F 7/00* | (2006.01) |

(Continued)

(52) U.S. Cl.
CPC .......... *A61C 19/066* (2013.01); *A61B 5/1468* (2013.01); *A61B 5/14507* (2013.01); *A61B 5/14539* (2013.01); *A61B 5/4277* (2013.01); *A61B 5/4547* (2013.01); *A61B 5/4839* (2013.01); *A61B 5/682* (2013.01); *A61B 5/742* (2013.01); *A61C 5/90* (2017.02); *A61F 7/00* (2013.01); *A61N 5/062* (2013.01);

(Continued)

(58) Field of Classification Search
CPC ........... A61C 19/063; A61C 5/14; A61C 5/90; A61C 19/003; A61C 19/066; A61N 5/0624; A61N 2005/0606; A61N 5/062; A61N 2005/0651; A61B 5/14507; A61B 5/1468; A61B 5/4277; A61B 5/4547; A61B 5/4839; A61B 5/682; A61B 5/742; A61F 7/00; A61F 2007/0017
See application file for complete search history.

(56) References Cited

U.S. PATENT DOCUMENTS

| | | |
|---|---|---|
| 5,674,182 A | 10/1997 | Suzuki et al. |
| 6,607,387 B2 | 8/2003 | Mault |

(Continued)

*Primary Examiner* — Nicholas Lucchesi
(74) *Attorney, Agent, or Firm* — H. Jay Spiegel

(57) ABSTRACT

A method employs a closed system mouthpiece using light and heat generation to activate a gel formulation to increase its volume. The gel formulation is coated into the mouthpiece, which is inserted into the user's mouth. Application of heat above a threshold temperature causes the gel to transform into foam and expand out of the mouthpiece and into the oral cavity. The mouthpiece creates a hermetic seal such that the foam expands out throughout the oral cavity into nooks and crannies that are normally difficult to access. Activation of a light source embedded within the mouthpiece enhances the bacteria killing properties of the foam material. The pH balance of the mouth is restored by the inventive method and apparatus to a neutral level in the range of 6.75 to 7.25.

25 Claims, 7 Drawing Sheets

(51) Int. Cl.
*A61N 5/06* (2006.01)
*A61B 5/1468* (2006.01)

(52) U.S. Cl.
CPC ............. *A61F 2007/0017* (2013.01); *A61N 2005/0606* (2013.01); *A61N 2005/0651* (2013.01)

(56) References Cited

U.S. PATENT DOCUMENTS

| | | | | |
|---|---|---|---|---|
| 6,860,879 B2 * | 3/2005 | Irion | ............ | A61B 5/0088 433/119 |
| 7,223,270 B2 | 5/2007 | Altshuler et al. | | |
| 7,223,281 B2 | 5/2007 | Altshuler et al. | | |
| 7,320,595 B2 * | 1/2008 | Duret | ............ | A61C 19/06 433/32 |
| 7,329,273 B2 | 2/2008 | Altshuler et al. | | |
| 7,329,274 B2 | 2/2008 | Altshuler et al. | | |
| 7,354,448 B2 | 4/2008 | Altshuler et al. | | |
| 7,422,598 B2 | 9/2008 | Altshuler et al. | | |
| 8,591,227 B2 * | 11/2013 | Levine | ............ | A61C 19/063 433/215 |
| 8,900,282 B2 * | 12/2014 | Brawn | ............ | A61N 5/0613 607/88 |
| 2004/0010299 A1 | 1/2004 | Tolkoff et al. | | |
| 2004/0247534 A1 * | 12/2004 | Stoltz | ............ | A61K 8/042 424/52 |
| 2005/0084826 A1 * | 4/2005 | Pilaro | ............ | A61C 5/00 433/215 |
| 2005/0113654 A1 | 5/2005 | Weber et al. | | |
| 2006/0019214 A1 * | 1/2006 | Lawrence | ............ | A61C 19/06 433/29 |
| 2006/0078848 A1 * | 4/2006 | Fischer | ............ | A61C 19/063 433/215 |
| 2007/0015112 A1 * | 1/2007 | Hochman | ............ | A61B 8/546 433/215 |
| 2007/0212661 A1 * | 9/2007 | Mehmet | ............ | A61C 19/063 433/32 |
| 2007/0259316 A1 * | 11/2007 | Conrad | ............ | A61C 19/06 433/215 |
| 2008/0003540 A1 * | 1/2008 | Khawaled | ............ | A61C 19/066 433/215 |
| 2008/0032252 A1 | 2/2008 | Hayman et al. | | |
| 2008/0233541 A1 | 9/2008 | De Vreese et al. | | |
| 2008/0255498 A1 * | 10/2008 | Houle | ............ | A61C 17/02 604/20 |
| 2009/0017422 A1 | 1/2009 | Creamer | | |
| 2009/0132011 A1 | 5/2009 | Altshuler et al. | | |
| 2009/0281433 A1 | 11/2009 | Saadat et al. | | |
| 2010/0081957 A1 | 4/2010 | Hyde et al. | | |
| 2011/0053173 A1 | 3/2011 | Hood et al. | | |
| 2012/0009539 A1 | 1/2012 | Goodson et al. | | |
| 2012/0021375 A1 | 1/2012 | Binner et al. | | |
| 2012/0123225 A1 | 5/2012 | Al-Tawil | | |
| 2012/0165694 A1 | 6/2012 | Meka et al. | | |
| 2012/0172677 A1 | 7/2012 | Logan et al. | | |
| 2012/0172678 A1 | 7/2012 | Logan et al. | | |
| 2012/0172679 A1 | 7/2012 | Logan et al. | | |
| 2012/0183919 A1 * | 7/2012 | Levine | ............ | A61C 19/063 433/29 |
| 2012/0189976 A1 * | 7/2012 | McDonough | ............ | A61C 17/0202 433/89 |
| 2012/0207806 A1 | 8/2012 | LoPesio | | |

\* cited by examiner

CLOSED SYSTEM MOUTHPIECE WITH LIGHT AND HEAT GENERATION TO ACTIVATE A FORMULATION TO INCREASE ITS VOLUME

This application is a Divisional of application Ser. No. 13/956,787, filed on Aug. 1, 2013. The present invention relates to a closed system mouthpiece with light and heat generation to activate a formulation to increase its volume.

BACKGROUND OF THE INVENTION

Most natural environments harbor an incredibly diverse collection of microbial species. Within these communities, bacteria compete with their neighbors for space and resources.

The mouth is no different, with a warm, nutrient rich environment, continuously bathed with saliva, and with a pH normally between 6.75-7.25, essentially neutral between acidic and basic. The oral cavity is a home for around 600 species and 8 billion bacteria all living together and vying for nutrients and resources to feed themselves, most of which are beneficial organisms and live in harmony with each other and the host.

How do all of these bacteria in one's mouth live together over time to maintain this natural healthy balance between good bacteria and the bad bacteria. Survival is key and the natural selection theory holds true over time. The microbiological community figures out how to live together, and not only survive, but to thrive in this natural ecosystem. The ability to work together and share the resources in their community is referred to as homeostasis, a balancing act that lives in our mouth in spite of numerous external changes.

However, when the external changes are too powerful for the homeostatic balance, the bacterial balance in the mouth shifts significantly. The bacteria that can cause harm begin to dominate the beneficial organisms. That is, shifts in the environment can throw the balance off between bacteria that have a positive effect vs. bacteria that cause disease. The three main environmental shifts are the pH of the mouth (acid and base balance), the availability of nutrients (food and resources) in our mouths, and how well we are cleaning the plaque off our teeth and gums; especially in the hard to reach places.

It is not the individual bacteria alone that cause disease, but the environment in our mouth that is altered by our diet and our ability to control plaque, both events we control by our daily actions. These actions directly affect the environmental circumstances in regulating and controlling the quality of the biofilm (bacterial plaque) in our mouths, the types of nutrients we put into our mouths, and the resulting pH.

For people who have a diet high in proteins (i.e., meat, processed foods) and simple carbohydrates or sugars, a low pH unhealthy, acidic environment is formed. This helps the acid tolerating bacteria like s. mutans that cause disease and displaces the oral-health associated, neutral pH bacteria such as s. salivarius. Another example of this phenomenon is the gram-negative anaerobic bacteria that also thrive in the more acidic environment that causes an inflammatory cascade to occur in the periodontal tissues and resulting gingivitis. Similarly, the bad breath causing bacteria that live in between the teeth and in the deep surfaces of the tongue also thrive in the acidic environment that decreases saliva flow and increases colonization of the harmful bacteria. So, by having a lower pH in our mouths because of what we put in our mouths and due to our food selection, the bacteria that cause decay, gum disease and bad breath start dominating the healthy bacteria. Couple this with poor plaque control, and the environment is now created for a shift in the bacterial populations to disease producing organisms and a bacterial load that not only impacts oral health, but overall health as well.

Today, the link between pathogenic bacteria originating in the oral cavity causing inflammation in other areas of the body has been scientifically demonstrated.

Dr. Han and her co-investigators have begun identifying the mechanisms that allow *F. nucleatum* to move from the mouth into the bloodstream and throughout the body—taking other bacteria with it and leaving destruction in their path (*Molecular Microbiology*, December 2011, Vol. 82:6, pp. 1468-1480). Her team has shown that *F. nucleatum* can induce preterm birth and stillbirth in animals and humans (see, for example, *Obstetrics & Gynecology*. February 2010, Vol. 115: suppl 2, part 2, pp. 442-445). Other researchers have linked this phenomenon to colorectal cancer (*Genome Research*, Oct. 18, 2011) and infections and abscesses in all the internal organs, including in the brain and lungs.

By controlling pH to maintain it within desirable limits, it is possible to alter the plaque biofilm, remineralize existing lesions and help prevent oral disease going forward.

Plaque is a very sticky substance that forms on the teeth in a matter of minutes and causes gum inflammation in a matter of days if the plaque is not timely removed. The areas in the mouth that are difficult to clean are the surfaces of the tongue and areas between the teeth that create an anaerobic environment. Without oxygen, the bacteria that cause bad breath and periodontal disease now colonize if they are not timely removed. If we look at ways to mitigate the dominance of the bad bacteria over the healthy ones, if we can impact the pH of our mouths and effectively decrease the bad bacteria in the mouth, we will have an effective way to promote good health in the mouth. The objective is to change the environment from oxygen poor-low pH sites where the pathogenic bacteria thrive to a safer, more effective way to rebalance homeostasis in the mouth toward enhanced health with an oxygen-rich-higher ph.

We know that only 10% of the population flosses regularly and that 75% of the population over the age of 35 has some form of gum disease. The latest data from the NIH and the Academy of Periodontics is that half the adult population has some form of periodontal disease, which is gum inflammation along with bone loss. These chronic type lesions are the ones that show an increase in bacterial load in the mouth which impacts areas all over the body as the oral disease bacteria have the chance to be disseminated to other areas in the body. The connection between oral health and overall health is an emerging science of oral systemic medicine and has been growing over the last decade. Moise Desvarieux, an infectious disease epidemiologist at Columbia University, conducted studies showing the link between chronic infections, including periodontal infections, and cardiovascular disease. Dr. Angela Kamer, Assistant Professor of Periodontology & Implant Dentistry at New York University, led a research team that found a connection between periodontal disease and cognitive function, citing higher levels of antibodies and inflammatory molecules associated with periodontal disease in Alzheimer's patients over healthy people. The British Medical Journal posted a study conducted by researchers at Brown University stating that individuals with high levels of Porphyromonas gingivalis bacterium had twice as great a risk of developing pancreatic cancer over individuals with lower levels of these bacterium.

Oral care products traditionally have focused on taking either a specific kill of a bacterium or to indiscriminately kill all bacteria. This thinking needs to be replaced with an approach that improves the environment to change the bacterial balance in the mouth in a safe way that will have a healthier and more balanced affect long term.

The use of light and heat in oral care is known to kill bacteria in the 470-490 nm wavelength range. The use of light alone will have an impact specifically on p. gingivalis and to eliminate this bacteria.

We also know that the light and antibacterial approaches attacking the organisms will only have a short term effect.

What has not been used in the past is a mouthpiece with light and heat built inside, that creates a sealed gasket effect for any formulation that will be placed inside of it. It would be advantageous to couple a mouthpiece with a formulation that changes a gel to foam when warmed along with the mouthpiece that has light and heat installed therein. A universally shaped mouthpiece allows for a custom fit as its internal flex circuit shapes to the user's mouth when they bite down on its platform area.

It would be advantageous for the light and heat of a mouthpiece to activate a formulation to transform it from a gel to foam. Such a foam increases in volume and as contained in the closed system mouthpiece drives its active ingredients to the very difficult areas that require meticulous plaque control. These areas between the teeth, furthest areas back in the mouth and on the tongue, need this level of diligence.

People have always had trouble routinely brushing and flossing which keeps the bacteria in a healthy balance of good vs. bad bacteria. Once the plaque is allowed to form on the teeth close to the gums, over the course of just a few days, the bacterial microflora change to the more pathogenic anaerobes that cause disease. The oral care regimen needs to be easy to use, short in duration, healthy and safe long term, and must fit into people's lifestyles. In the past, minutes of brushing and 2 minutes to floss has not seen great success because of the technique sensitivity (user's ability) and the amount of time required to fit into people's busy lifestyles.

Applicant's original invention involves incorporation of light and heat to optimize the effectiveness of a whitening formulation by keeping the actives around longer and pushing them into the hard to reach areas to whiten. This mouthpiece has a warming element with a TPR or other thermoplastic material that warms, softens, and conforms to the mouth upon use to create a peripheral seal around the outside of the mouthpiece to seal actives inside. The universal mouthpiece, because of the flexible circuits, fits to any mouth, any arch form and the thermoplastic material forms the peripheral seal closed system.

The mouth is a dark, moist environment, where the hard to reach areas are void of oxygen, creating the perfect living headquarters for the anaerobic bacteria that thrive and cause the most damage.

It is known in the prior art to measure the level of acidity or basic characteristic within a person's mouth. However, Applicant is unaware of any prior art teaching measuring of the pH in the mouth of a user in the manner contemplated in the present invention. Applicant is aware of the following prior art:

| U.S. Published Patent Applications | |
|---|---|
| 2005/0113654 to Weber et al. | 2011/0053173 to Hood et al. |
| 2008/0233541 to De Vreese et al. | 2012/0123225 to Al-Tawil |
| 2009/0017422 to Creamer | 2012/0165694 to Meka et al. |
| 2009/0132011 to Altshuler et al. | 2012/0172677 to Logan et al. |

-continued

| U.S. Published Patent Applications | |
|---|---|
| 2009/0281433 to Saadat et al. | 2012/0172678 to Logan et al. |
| 2010/0081957 to Hyde et al. | 2012/0172679 to Logan et al. |

| U.S. Patents | |
|---|---|
| 5,674,182 to Suzuki et al. | 6,607,387 to Mault. |

While each of these references teaches some aspect of sensing pH, none of them teaches the manner of doing so contemplated in the present invention.

Generally speaking, it is known in the prior art to utilize light at desired wavelengths to kill orally located germs. Applicant is aware of the following prior art references:

| U.S. Published Patent Applications | |
|---|---|
| 2004/0010299 to Tolkoff et al. | 2012/0021375 to Binner et al. |
| 2008/0032252 to Hayman et al. | 2012/0207806 to LoPesio. |
| 2012/0009539 to Goodson et al. | |

| U.S. Patents | |
|---|---|
| 7,223,270 to Altshuler et al. | 7,329,274 to Altshuler et al. |
| 7,223,281 to Altshuler et al. | 7,354,448 to Altshuler et al. |
| 7,329,273 to Altshuler et al. | 7,422,598 to Altshuler et al. |

The prior art references listed above generally disclose the use of light to kill bacteria, the use of light intra-orally, the use of the combination of mouthpieces and solutions to kill mouth bacteria, and the use of light in a toothbrush for oral phototherapy. Hayman et al. disclose use of a mouthpiece and use of light to kill bacteria.

While these references teach the concept of using light to kill bacteria in the mouth, in a general sense, none of these references taken alone or in combination with other references teaches or suggests the specific manner by which the present invention employs a mouthpiece, heat and light, and a foaming substance within a hermetically sealed environment to retain or restore an advantageous pH level within the mouth of a user to maintain oral health and general health.

SUMMARY OF THE INVENTION

The present invention relates to a closed system mouthpiece with light and heat generation to activate a formulation to increase its volume. The present invention includes the following interrelated objects, aspects and features:

(1) The present invention employs a gel formulation that may be coated into a mouthpiece, the mouthpiece subsequently being inserted into the mouth of the user.

(2) Application of heat above a threshold temperature causes the gel to transform into foam and expand out of the mouthpiece and into the oral cavity.

(3) The mouthpiece is specifically designed to create a hermetic seal such that the mouth behind the teeth is transformed into a sealed chamber. Thus, when the application of heat causes the gel to expand into foam, the foam expands out throughout the oral cavity into nooks and crannies that are normally difficult to access.

(4) With the foam so dispersed within the oral cavity, activation of a light source embedded within the mouthpiece enhances the bacteria killing properties of the now foam material. This sealing property of the mouthpiece is described by Applicant as a "gasket effect."

(5) The foam spreads onto the tongue of the user as well and acts to kill any damaging bacteria found there. As a result of operation of the present invention, the pH balance of the mouth is restored to a neutral level in the range of 6.75 to 7.25 or maintained at that pH level in which a healthy balance is maintained between various species of bacteria. With damaging bacteria killed through use of the mouthpiece and the gel transforming into foam, the pipeline feeding damaging bacteria throughout the body is cut off, thereby enhancing overall health of the user.

As such, it is a first object of the present invention to provide a mouthpiece with integral light and heat sources to facilitate illuminating and heating the inside of the mouth of a user.

It is a still further object of the present invention to provide such a device in which a gel may be coated, which gel expands into foam when exposed to heat above a threshold temperature.

It is a still further object of the present invention to provide such a mouthpiece including structure to create a hermetic seal about the teeth and gums of the user to seal the oral cavity from outside the mouth to fulfill the purposes of the present invention. The structure of the gasket effect of the mouthpiece includes a peripheral flange that creates a "gasket flange" that has a wiper blade and a rolled peripheral seal to ensure a tight seal to create a sealed environment.

It is a yet further object of the present invention to provide such a system in which the foam expands throughout the oral cavity to kill anaerobic bacteria (bacteria that live without oxygen) in the hard to reach places and restore the pH of the mouth to within a healthy range.

It is a yet further object of the present invention to activate a source of light within the mouthpiece to perform additional therapeutic functions.

It is a yet further object of the present invention to provide such a mouthpiece in which a pH sensor is integrally mounted to facilitate close monitoring of the pH of the mouth to fulfill the therapeutic purposes of the present invention. The pH sensor will tell the wearer when their mouth is healthy, and using specific formulations will improve the overall health through pH detection.

These and other objects, aspects and features of the present invention will be better understood from the following detailed description of the preferred embodiments when read in conjunction with the appended drawing figures.

SPECIFIC DESCRIPTION OF THE PREFERRED EMBODIMENT

Figure 1:
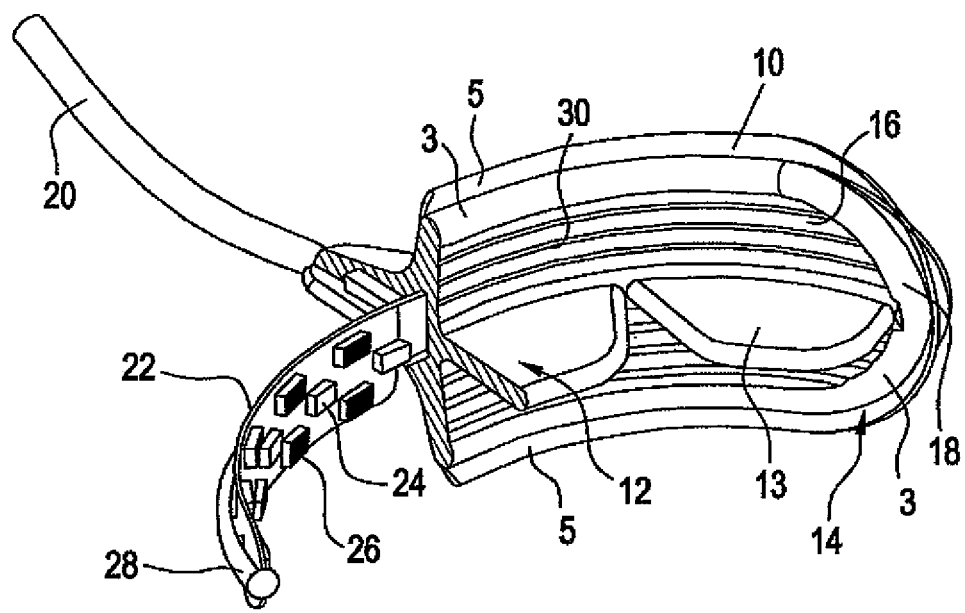
FIG. 1 shows a perspective view of the inventive mouthpiece with portions broken away to show details of the embedded flexible circuit.
Figure 2:
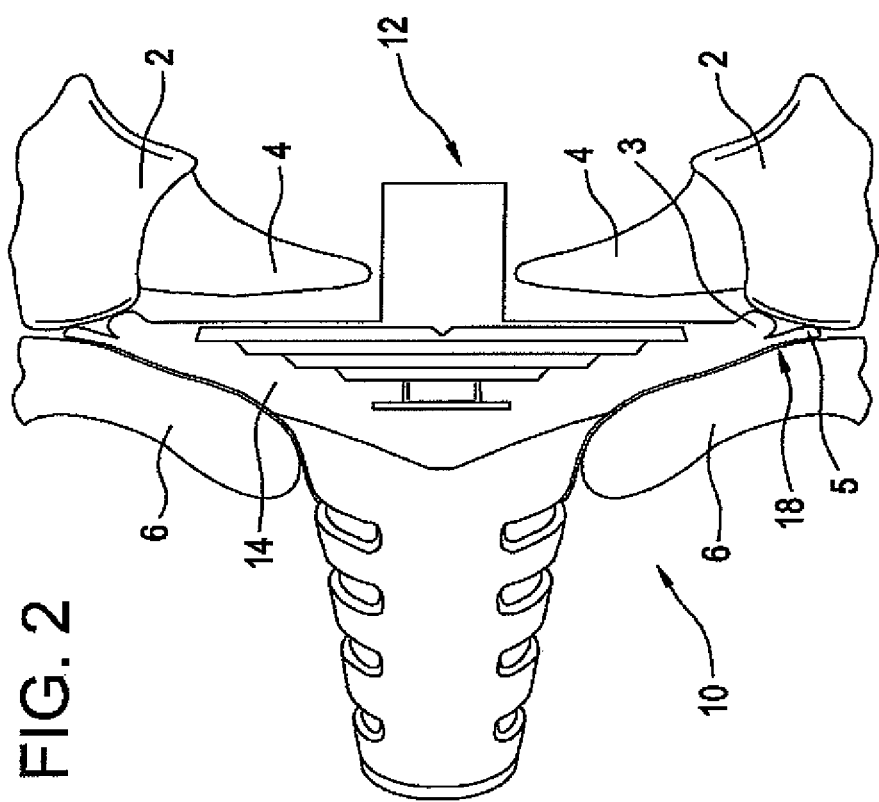
FIG. 2 shows a cross-sectional view which depicts how the flexible circuit is located embedded within the mouthpiece and the mouthpiece effects a hermetic seal of the oral cavity.

With reference first to FIGS. 1 and 2, the inventive mouthpiece is generally designated by the reference numeral 10 and includes a bite surface 12, central and perpendicular to the main body 14, and which extends outwardly from a central portion of the inner surface of the main body on one side thereof as best seen in FIG. 2. The bite surface 12 is configured to ensure stability of the mouthpiece 10 when it is positioned in the user's mouth between the upper and lower arches. The bite surface 12 may be formed from two or more segmented or separated portions, or, alternatively can be made of a single continuous bite surface 13. The segmented bite surface is preferred because it better allows for adjustments in the curvature of the mouthpiece 10 to more easily adapt to mouths of differing shapes and configurations. The mouthpiece includes a double seal bead 18 (FIGS. 1 and 2) extending about its periphery that is designed to seal at just above the gum margins to provide a hermetic sealed environment within the oral cavity when the mouthpiece is in place. The double seal bead includes a seal bead 3 and a wiper blade 5. These seals extend about the periphery of the mouthpiece 10 and seal at the margin of the gums 2, thereby creating a closed chamber in the oral cavity, isolating the teeth 4 from the atmosphere. The lips 6 of the user lie over the body of the mouthpiece as seen in FIG. 2 to further enhance sealing effect. A plurality of textured bands 16 (FIG. 1) are also provided, specifically designed to channel LED light more diversely over the entirety of the teeth and oral cavity. The bite surface 12 is specifically designed to be transparent so that light from the LEDs embedded within the mouthpiece (as will be described in greater detail hereinafter) and co-planar with the bite surface 12 can find its way behind the teeth and into the oral cavity for purposes to be described in greater detail hereinafter. As explained above, reflective surfaces within the mouthpiece enhance light transmission and its spread within the oral cavity. Reflective surfaces are also provided in the mouthpiece to guide light from the LEDs 24 into the oral cavity.

Embedded within the mouthpiece 10 is a flexible circuit board 22 that has integrally mounted therein two rows of heat generating resistors 26 between which is a single row of illuminating LEDs 24. The flexibility of the circuit board 22 permits the mouthpiece 10 to be bent to adapt to differing curvatures and configurations of differing user mouths. In the preferred embodiment of the present invention, the inner surface 30 of the mouthpiece above and below the bite surface 12 is tilted inward at an angle in the range of 5 to about 15 degrees to enhance the seal of the peripheral bead 18. This is seen with particular reference to FIG. 2 which shows, schematically, a tooth 34 as well as the gum 35 with the seal bead 18 sealing at the margin between the tooth 34 and the gum 35 so that beams of light 32 impinge upon all of the tooth surfaces, in use. Reference numeral 20 depicts an electrical conductor which supplies power to the flexible circuit board 22 from a source of power not shown in FIGS. 1 and 2. Many of the details described above are also found in Applicant's prior U.S. Pat. No. 8,371,853, the details of which are incorporated by reference herein.

The inventive mouthpiece disclosed in U.S. Pat. No. 8,371,853 was disclosed as principally usable for teeth whitening. It was also disclosed as usable in methods of desensitizing teeth, accelerating healing of mouth sores or ulcerations, for treating gum disease or freshening a patient's breath. The present invention expands upon the uses contemplated in Applicant's prior mouthpiece invention by operating in conjunction with a formulation usable for other purposes.

In particular, the present invention is intended to be used in connection with a gel formulation which when heated above a threshold temperature transforms into foam dramatically expanding its volume and spreading throughout the oral cavity for the purposes disclosed herein. Such a gel may include as constituent ingredients including PEG-8, propylene glycol, canola oil, hydrogen peroxide, glycerin, dimethylisosorbide, a formulation of poloxamer ascorbic acid, xylitol, and other substances including flavoring and coloration. In essence, the substance employed may be spread over the surfaces of the mouthpiece and maintains its gel consistency at room temperature. However, when placed in the mouth, the mouth temperature begins to raise the temperature of the gel. When the heating resistors 26 are activated, they elevate the temperature of the mouth over 100° F. At the designed temperature threshold, the gel begins to expand, transforming into foam that begins to spread throughout the oral cavity coating all of the tooth surfaces as well as the surfaces of the oral cavity including the tongue, the roof of the mouth, interstices between teeth and gums, and other hard to reach areas. In the preferred embodiment, the gel begins to slowly transform into foam at the normal temperature of the oral cavity, 37° C. With the heating resistors 26 activated, at 40° C., the transformation speeds up. The heating resistors 26 can heat the oral cavity to up to about 50° C., a high enough temperature to quickly transform the gel into foam without making the user uncomfortable from the heat.

Figure 3:
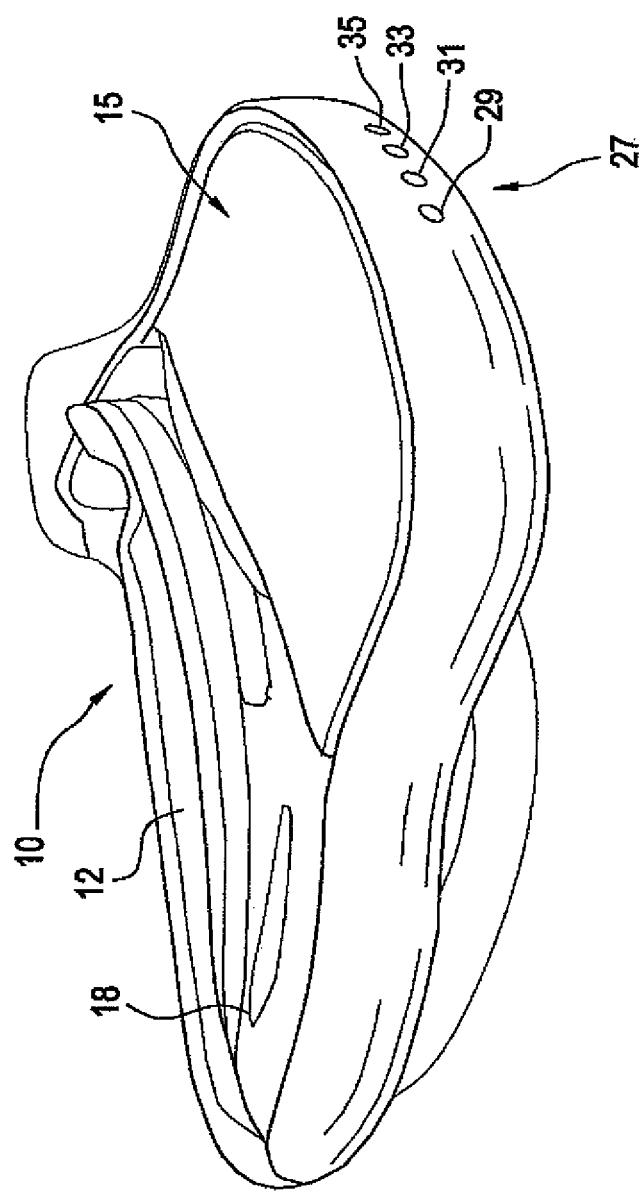
FIG. 3 shows a further perspective view of the inventive mouthpiece showing further details including those of aspects of its pH sensor.
Figure 4:
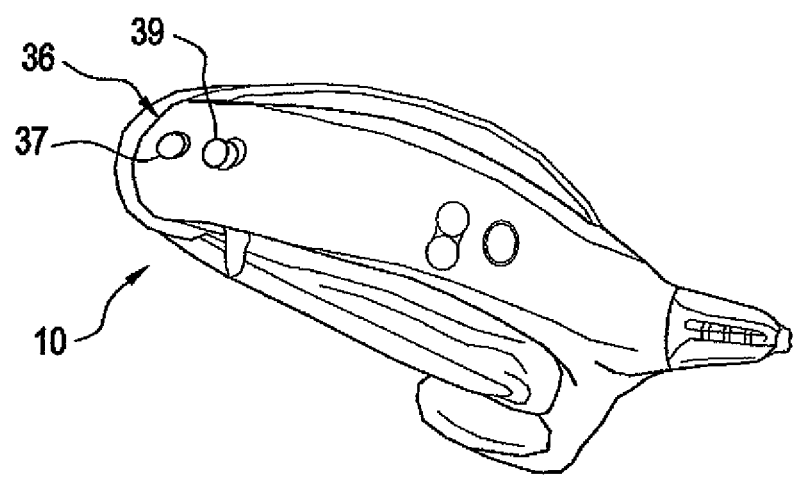
FIG. 4 shows a side view of the inventive mouthpiece showing the electrodes of the pH sensor.
Figure 5A:
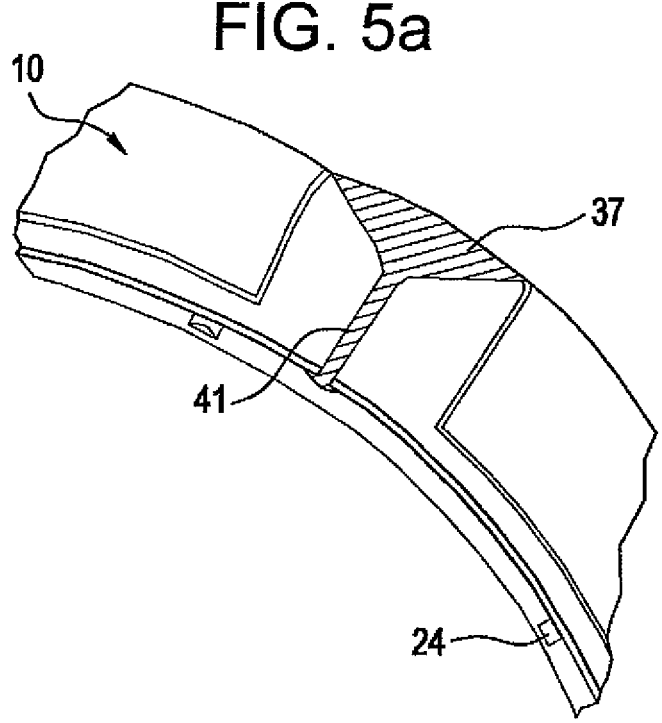
FIG. 5a shows a schematic representation of some of the circuitry of the inventive mouthpiece.

With reference to FIGS. 3, 4 and 5a, the mouthpiece 10 has a gripping tab 15 that may be gripped by the user in placing the mouthpiece 10 within the oral cavity. The gripping tab 15 also includes a display 27 that includes a series of lights 29, 31, 33 and 35. Those lights comprise a display used in conjunction with a pH sensor incorporated into the inventive device. With reference to FIG. 4, the electrodes 37 and 39 are located on the mouthpiece 10 in a location in which they are consistently immersed in saliva. The saliva between the electrodes 37 and 39 closes an electrical circuit that may be measured as a voltage that corresponds to the pH of the oral cavity. FIG. 5a shows the electrode 37 embedded within the mouthpiece 10 and including a conductor 41 preferably made of a material such as copper.

In more detail, the pH sensor electrodes 37 and 39 are made of a pH sensitive material and are electrically connected to the flexible circuit board 22. The preferred location for the electrodes is at either end of the arch of the mouthpiece 10. The electrodes may be made of any solid material that develops hydrogen ion dependent electrical potentials. Such materials include Iridium Oxide, Silver Chloride, Graphene, Carbon Nanotubes, and other Nano materials.

As the electrodes are exposed to saliva, they develop a measurable electrical potential. The electrical potential on the electrodes is measured as a voltage and correspondingly increases or decreases responsive to the pH value of the saliva. The voltage measured at the sensor is computed by a microprocessor in the mouthpiece and converted into an indication of the pH. The measured pH is displayed by the color coded lights 29, 31, 33 and 35 of the display 27, in one embodiment thereof. In one embodiment of color-coded indicator lights, a green indicator light can be used to signify a pH of saliva within a healthy range, for example, 6.75 to 7.25. A red indicator light can be used to signify a pH of saliva in an unhealthy range, for example, below 6.75. In another variation, the red and green lights can be programmed to illuminate responsive to other pH ranges. Thus, the green light can be illuminated to signify a healthy pH for saliva where the pH is 7.0 or higher, and the red light can be illuminated to signify a saliva pH of below 7.0. In another embodiment, the display can be separate from the mouthpiece and the microprocessor can be connected to the display via a remote wired or wireless link. In either embodiment, a preferred manner of practicing the present invention is to measure the pH of saliva in the user's oral cavity before the mouthpiece is coated with gel and before the LEDs and heating resistors are activated. In this way, the baseline measurement of pH before treatment can be established so that restoration of the pH to a healthy range can be demonstrated. As is well known by those of ordinary skill in the art, pH below 7.0 signifies acidic saliva which demonstrates the existence of active disease. Through practice of the present invention, the pH of saliva in the oral cavity is elevated to a neutral pH signifying a healthy oral cavity.

In more detail, it is well known by those of ordinary skill in the art that the pH of a liquid can be measured by employing two spaced electrodes. As explained in *WHAT IS pH, AND HOW IS IT MEASURED? A Technical Handbook for Industry*, by Frederick J. Kohlmann, © 2003 Hach Company (which is incorporated by reference herein), in the 19$^{th}$ century, Hermann Walther Nernst introduced the Nernst equation which resulted in definition of the Nernst factor which provides the amount of change in total potential for every ten-fold change in ion concentration. In essence, Nernst determined that for every pH unit change, the total electrical potential will change by 59.16 mV.

With this information in mind, Kohlmann describes the use of a pair of electrodes, one of which is a reference electrode, and the other of which is a measuring electrode. When the measured potential between these two electrodes is zero, this equates to a pH measurement of 7.0, neutral pH. As the solution becomes more acidic (a pH below 7), the mV potential becomes more negative at a rate of 59.16 mVs for every unit reduction in the pH value. Thus, a voltage reading of −59.16 mVs equates to a pH of 6.0. Conversely, as the solution becomes more basic (a pH above 7), the mV potential becomes more positive at a rate of 59.16 mVs for every unit increase in the pH value. Thus, a voltage reading of +59.16 mVs equates to a pH of 8.0. With this information in hand, it is easy to see how one of ordinary skill in the art can devise a display, whether analog, digital, or employing indicator lights, to indicate to the user the pH of saliva within the oral cavity of the user, which saliva immerses the spaced electrodes.

Figure 5B:
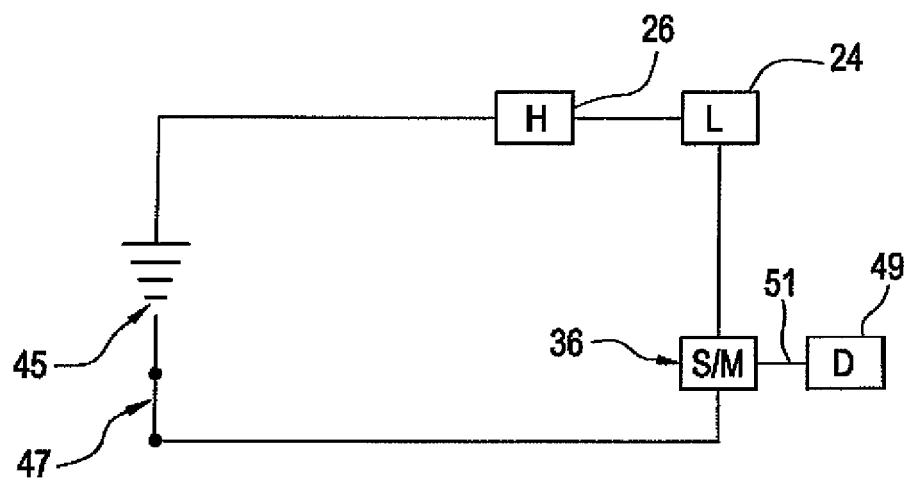
FIG. 5b shows a circuit diagram of one embodiment of circuitry.
Figure 5C:
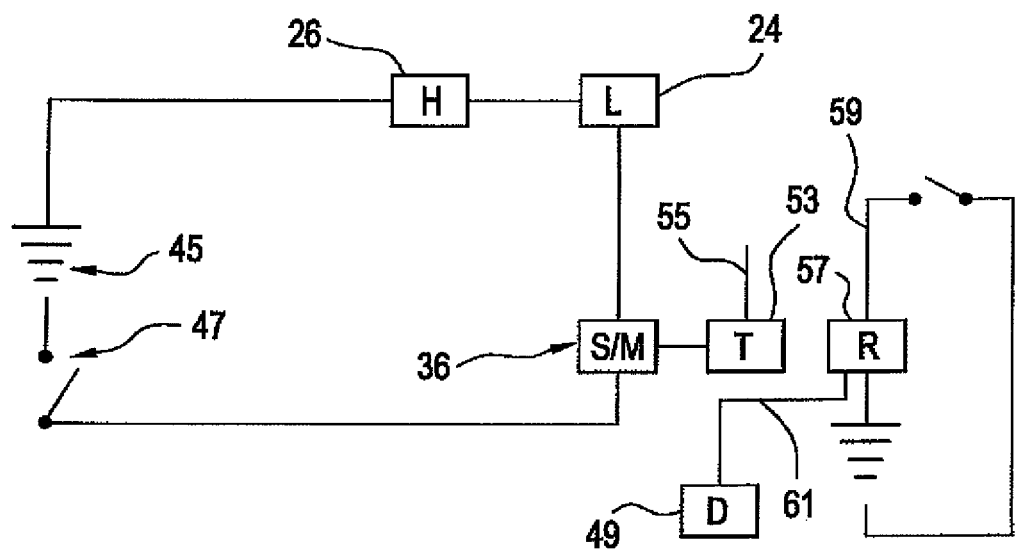
FIG. 5c shows a circuit diagram of a second embodiment of circuitry.

With reference to FIGS. 5b and 5c, two examples of electrical circuitry usable in connection with the present invention are schematically shown. With reference to FIG. 5b, a source of power is schematically shown referred to by reference numeral 45. This may comprise a battery contained within the mouthpiece 10 or, alternatively, the source of power remotely located and connected via the conductor 20 (FIGS. 1 and 2). In either event, an on-off switch 47 controls activation and deactivation of the system. In FIGS. 5b and 5c, the heating resistors 26 and LED 24 are schematically shown. Reference numeral 36 refers to a combination sensor microprocessor while the associated display is referred to with reference numeral 49. In the circuit of FIG. 5*b*, the microprocessor is connected to the display via a hard wired electrical conductor 51. In the embodiment of FIG. 5*c*, the microprocessor is connected to a transmitter 53 which has an antenna 55 that transmits signals corresponding to the pH via the antenna 55 to a receiver 57 antenna 59 which then provides the information via a conductor 61 to the display 49.

With reference to FIGS. 6-17, the manner of operation of the present invention in its preferred mode of operation will now be described.

Figure 6:
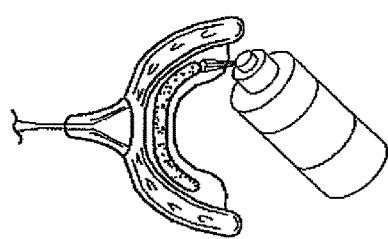
FIGS. 6-17 show the sequence of intended operation of the inventive mouthpiece.
Figure 7:
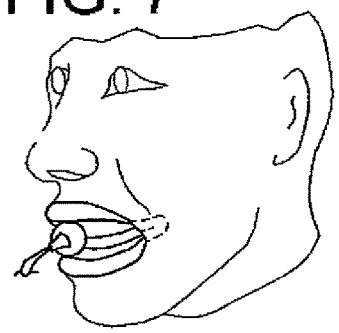

With reference to FIG. 6, gel from a canister thereof is applied to the upper and lower areas of the mouthpiece 10 above and below the bite surface 12. With reference to FIG. 7, the mouthpiece is inserted into the mouth and the LEDs 24 and heat resistors 26 are activated.

Figure 8:
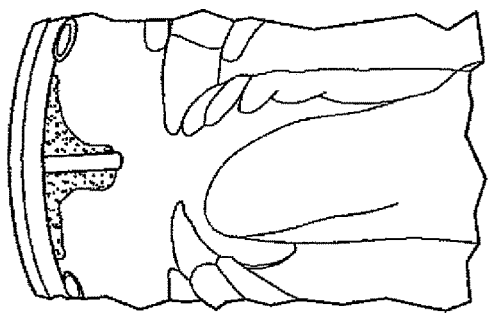
Figure 9:
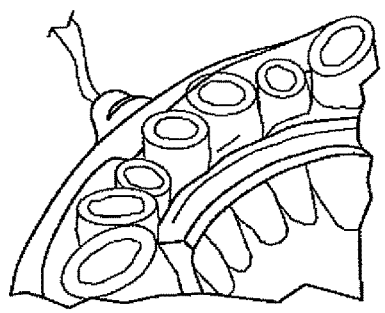

With reference to FIGS. 8 and 9, the peripheral bead 18 of the mouthpiece 10 creates a seal at the margin between the teeth and gums so that the oral cavity of the user is completely sealed off from the outside environment.

Figure 10:
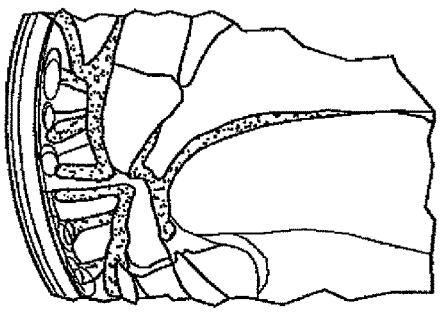
Figure 11:
Figure 12:
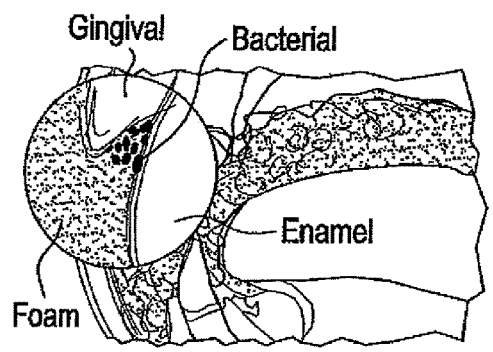
Figure 13:
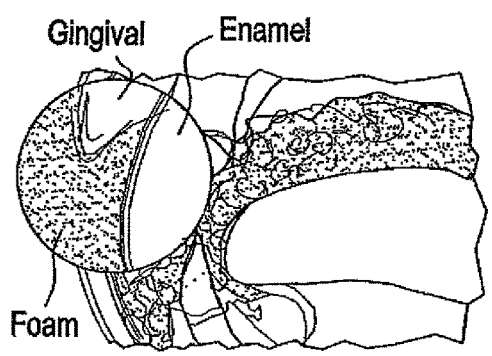
Figure 14:
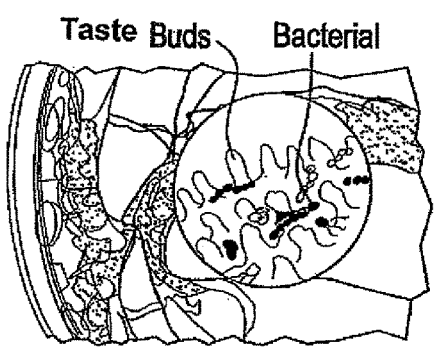
Figure 15:
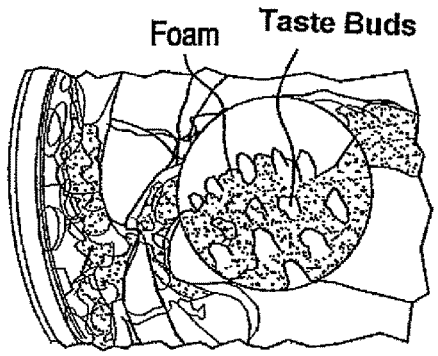
Figure 16:
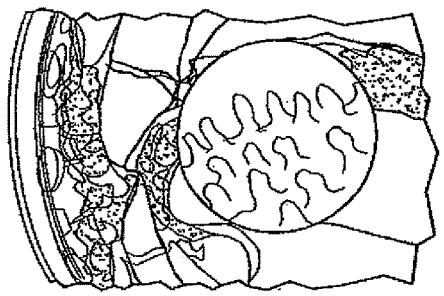
Figure 17:
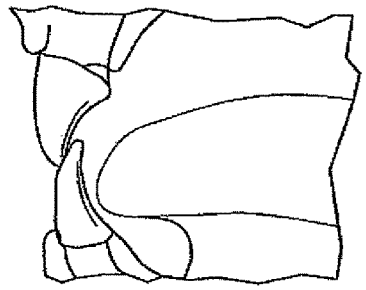

With reference to FIGS. 10-11, when the temperature of the oral cavity rises above a threshold temperature, typically over 100 degrees F., the gel transforms into foam and expands over the teeth, gums, roof of the mouth, tongue, and other areas and interstices of the oral cavity.

With reference to FIGS. 12-15, the foam kills off undesirable bacteria from the tooth enamel, tongue, and other oral cavity surfaces. As a result, the tongue, teeth, and oral cavity are cleansed of harmful bacteria and the pH of the oral cavity rises to the healthy range of 6.75 to 7.25. The pH of the oral cavity is continually monitored during the process via the display 27 (FIG. 3) or 49 (FIGS. 5*b* and 5*c*). In the display 27, each light corresponds to a unique pH or pH range. Once the pH of the oral cavity has been restored to within the healthy range, the mouthpiece 10 may be deactivated and removed from the mouth and the oral cavity may be rinsed to remove the foam therefrom.

Treatments such as that which is described above may be repeated on a daily basis or multiple times during a day to maintain the pH of the oral cavity within a healthy range to not only enhance the health of the user's oral cavity, but to enhance health generally.

The present invention takes a unique formulation that works in conjunction with the closed system mouthpiece that has heat and light activating the gel to increase volume and change into a foam. This foam can expand against the walls of the oral cavity and push its contents into these dark, oxygen poor areas where the "bad" bacteria thrive. The objective is to change the environment from oxygen poor-low pH loving sites where the pathogenic bacteria thrive to a safer, more effective way to rebalance homeostasis in the mouth towards health.

Applicant has devised four separate formulations of gels that effectively fulfill the objects and purposes of the present invention. A first formulation includes a mixture of PEG-8, Propylene Glycol, Canola Oil, PVP-Hydrogen Peroxide K-90 (1.7% peroxide), Glycerin, Dimethyl Isosorbide, Poloxamer 407, Ascorbic Acid, Green Tea Extract, Vitis Vinifera (Grape Seed) Extract, Sodium Bicarbonate, Flavor, Xylitol, and Aqua. A second formulation includes a mixture of PEG-8, Propylene Glycol, Canola Oil, PVP-Hydrogen Peroxide K-30 (1.7% peroxide), Glycerin, Dimethyl Isosorbide, Poloxamer 188, Xylitol, Ascorbic Acid, Green Tea Extract, Vitis Vinifera (Grape Seed) Extract, Flavor, and Aqua. A third formulation includes a mixture of PEG-8, Propylene Glycol, Canola Oil, Glycerin, PVP-Hydrogen Peroxide K-90, Dimethyl Isosorbide, PVP-Hydrogen Peroxide K-30, Xylitol, Poloxamer 188, Flavor, Potassium Olivoyl Hydrolyzed Oat Protein, Sorbitol, Tocopheryl Acetate, Tetrahexyldecyl Ascorbate, Green Tea Extract, Vitis Vinifera (Grape Seed) Extract, Aqua, Mica, Titanium Dioxide, Sodium Bicarbonate, Hydrogenated Cotton Seed Oil, and Potassium Chloride. A fourth formulation includes a mixture of PEG-8, Propylene Glycol, Canola Oil, Glycerin, PVP-Hydrogen Peroxide K-90, PVP-Hydrogen Peroxide K-30, Fumed Silica (Vendor #2), Dimethyl Isosorbide, Potassium Olivoyl Hydrolyzed Oat Protein, Stevia Glucosides, Tocopheryl Acetate, Hydrogenated Cotton Seed Oil, Tetrahexyldecyl Ascorbate, Xylitol, Flavor (Flavorchem), Sorbitol, Aqua, Sodium Bicarbonate, Potassium Chloride, Mica, and Titanium Dioxide.

The invention defines a mouthpiece that uses light and heat in a closed system and a peripheral seal that works in conjunction with a formulation that transforms from a gel to a foam upon application of heat. Once the foam expands into a closed system, the gasket effect of the closed container seals all contents and optimizes the formulation's effect. The gasket seal 3, 5 gives an additional layer of protection to prevent oxygen escape at the periphery of the mouthpiece where it meets the soft tissue of the gums and the lips.

There is a desire to change the pH of the mouth with a formulation that deodorizes the mouth and oxygenates the teeth and gums thereby decreasing the population of the anaerobic gram negative bacteria that causes gum disease, bad breath and tooth sensitivity. By raising the pH, the acid producing bacteria of decay will also be arrested in this more favorable environment.

As such, an invention has been disclosed in terms of a preferred embodiment thereof as well as a preferred manner of use, that fulfill each and every one of the objects of the invention as set forth hereinabove, and provide a new, useful and unobvious closed system mouthpiece with light and heat generation to activate a formulation to increase its volume, of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A method of treating an oral cavity of a user, including the steps of:
   a) providing a mouthpiece in which at least one heat source is embedded and connectable to a source of power;
   b) said mouthpiece including a peripheral sealing member comprising two concentric sealing members;
   c) coating rearward facing surfaces of said mouthpiece with a gel;
   d) inserting said mouthpiece into said oral cavity with said sealing member sealing said oral cavity;
   e) activating said at least one heat source and raising temperature of said gel until said temperature reaches a threshold temperature at which said gel transforms into a foam and spreads within said oral cavity;
   f) maintaining said mouthpiece sealing said oral cavity for a desired time period;
   g) after said desired time period has expired, removing said mouthpiece and rinsing said oral cavity.

2. The method of claim 1, further including the step of providing said mouthpiece with a bite tab extending rearwardly central of a main body of said mouthpiece, said bite tab having upper and lower surfaces engageable by a user's teeth.

3. The method of claim 1, wherein said concentric sealing members comprise a first peripheral seal comprising a seal bead and a second peripheral seal comprising a wiper blade.

4. The method of claim 3, wherein said wiper blade is concentrically outside said seal bead.

5. The method of claim 2, wherein said main body also contains at least one light source embedded therein.

6. The method of claim 5, further including the step of providing a flexible circuit board embedded within said main body and carrying said at least one heat source and at least one light source.

7. The method of claim 6, wherein said at least one heat source comprises an array of heat sources.

8. The method of claim 7, wherein said at least one light source comprises an array of light sources.

9. The method of claim 1, further including the step of providing said mouthpiece with a pH sensor immersible in saliva within said oral cavity.

10. The method of claim 9, further including the step of providing said pH sensor with an indicator indicating pH value within said oral cavity.

11. The method of claim 10, further including the step of monitoring pH in said oral cavity and removing said mouthpiece from said oral cavity when said pH value is within a desired range.

12. The method of claim 11, wherein said desired range is 6.75 to 7.25.

13. The method of claim 11, wherein after said removing step, said method includes the step of rinsing said oral cavity.

14. The method of claim 10, wherein said indicator is carried by said mouthpiece.

15. A method of treating an oral cavity of a user, including the steps of:
 a) providing a mouthpiece in which at least one heat source and at least one light source are embedded and connected to a source of power;
 b) said mouthpiece including a peripheral sealing member and a central bite tab extending rearwardly;
 c) coating rearward facing surfaces of said bite tab with a gel;
 d) inserting said mouthpiece into said oral cavity, with said sealing member sealing said oral cavity;
 e) activating said at least one heat source and raising temperature of said gel until said temperature reaches a threshold temperature at which said gel transforms into a foam and spreads within said oral cavity;
 f) maintaining said mouthpiece sealing said oral cavity;
 g) measuring pH of said oral cavity, and when pH of said oral cavity is within a desired range, removing said mouthpiece and rinsing said oral cavity.

16. The method of claim 15, wherein said peripheral sealing member comprises two concentric sealing members, a first peripheral seal comprising a seal bead and a second peripheral seal comprising a wiper blade.

17. The method of claim 15, further including the step of providing a flexible circuit board embedded within said main body and carrying said at least one heat source and said at least one light source.

18. The method of claim 17, wherein said at least one heat source comprises an array of heat sources and said at least one light source comprises an array of light sources.

19. The method of claim 15, further including the step of providing said mouthpiece with a pH sensor immersible in saliva within said oral cavity, said pH sensor being provided with an indicator indicating pH value within said oral cavity.

20. A method of treating an oral cavity of a user, including the steps of:
 a) providing a mouthpiece in which at least one heat source is embedded and connectable to a source of power;
 b) said mouthpiece including a peripheral sealing member;
 c) coating rearward facing surfaces of said mouthpiece with a gel;
 d) inserting said mouthpiece into said oral cavity with said sealing member sealing said oral cavity;
 e) activating said at least one heat source and raising temperature of said gel until said temperature reaches a threshold temperature at which said gel transforms into a foam and spreads within said oral cavity;
 f) maintaining said mouthpiece sealing said oral cavity for a desired time period;
 g) after said desired time period has expired, removing said mouthpiece and rinsing said oral cavity; and
 h) further including the step of providing said mouthpiece with a pH sensor immersible in saliva within said oral cavity.

21. The method of claim 20, further including the step of providing said pH sensor with an indicator indicating pH value within said oral cavity.

22. The method of claim 21, further including the step of monitoring pH in said oral cavity and removing said mouthpiece from said oral cavity when said pH value is within a desired range.

23. The method of claim 22, wherein said desired range is 6.75 to 7.25.

24. The method of claim 22, wherein after said removing step, said method includes the step of rinsing said oral cavity.

25. The method of claim 21, wherein said indicator is carried by said mouthpiece.

* * * * *